United States Patent [19]

Cale, Jr.

[11] 4,327,107

[45] Apr. 27, 1982

[54] METHOD USEFUL IN THE TREATMENT OF SUGAR CATARACTS USING 4-SUBSTITUTED-2-IMINOIMIDAZOLIDINE COMPOUNDS

[75] Inventor: Albert D. Cale, Jr., Mechanicsville, Va.

[73] Assignee: A. H. Robins Company, Inc., Richmond, Va.

[21] Appl. No.: 146,608

[22] Filed: May 5, 1980

Related U.S. Application Data

[62] Division of Ser. No. 9,899, Feb. 6, 1979, Pat. No. 4,247,705.

[51] Int. Cl.$^3$ ............... A61K 31/415; A61K 31/495; A61K 31/445
[52] U.S. Cl. .................. 424/273 R; 424/248.56; 424/250; 424/267
[58] Field of Search .................. 424/248.56, 250, 267, 424/273

[56] References Cited

U.S. PATENT DOCUMENTS 3,147,270  9/1964  Anderson .................. 548/315

*Primary Examiner*—Sam Rosen

[57] ABSTRACT

This invention provides a novel class of 2-iminoimidazolidines which include 4-substituted derivatives such as 4-(2-chloroethyl)-1-methyl-2-methylimino-3-phenyl imidazolidine fumarate:

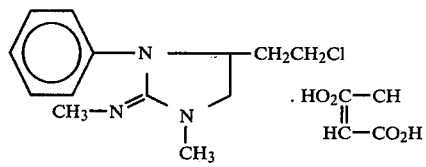

This illustrated 4-substituted 2-iminoimidazolidine compound exbibits cardiovascular hypotensive, hypoglycemic (glucose tolerance, and sugar cataract) and anti-inflammatory (pleural effusion) pharmacological activities in test animals.

7 Claims, No Drawings

METHOD USEFUL IN THE TREATMENT OF SUGAR CATARACTS USING 4-SUBSTITUTED-2-IMINOIMIDAZOLIDINE COMPOUNDS

This is a division of application Ser. No. 9,899, filed Feb. 6, 1979 now U.S. Pat. No. 4,247,705, issued Jan. 27, 1981.

BACKGROUND OF THE INVENTION

There are a number of organic compounds listed in the chemical literature which contain a 2-iminoimidazolidine nucleus:

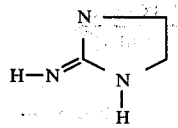

Among the known compounds are 1-[p-(2-aminoethyl)-phenylsulfonyl]-3-butyl-4-ethyl-2-iminoimidazolidine and 1-cyclohexyl-2-imino-4-methyl-3-(p-tolylsulfonyl)imidazolidine.

Another known 2-iminoimidazolidine compound is enduracididine, an aminoacid which is derived from enduracidin by acid hydrolysis (J. Antibiot. (Tokyo), 21 655 (1968), and which has the following structure formula:

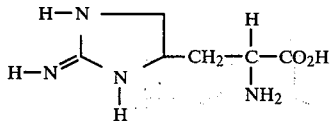

Other 2-iminoimidazolidine compounds are listed in the chemical literature which are interesting from the viewpoint of potentially useful pharmacodynamic properties. Such listed compounds include 2-imino-1,3-diphenylimidazolidine and 1-(p-chlorophenyl)-3-dodecyl-2-iminoimidazolidine.

One compound, 2-imino-1-methyl-3-phenylimidazolidine hydrochloride, has the following structure:

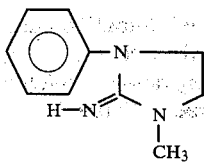

This compound was screened for hypotensive and antiarrhythmic and other pharmacodynamic activities. The said 2-iminoimidazolidine compound exhibited antiarrhythmic activity, but was inactive with respect to hypoglycemic and anti-inflammatory properties. Further, the compound exhibited hypertensive rather than hypotensive activity.

Accordingly, it is an object of this invention to provide a novel class of 2-iminoimidazolidine derivatives characterized by one or more pharmacological properties which qualify the said derivatives as prospective active agents in diverse pharmaceutical preparations for the treatment of cardiovascular hypertension, cardiac arrhythmia and/or hyperglycemia, and related conditions which are responsive to the 2-iminoimidazolidine active agents.

Other objects and advantages shall become apparent from the accompanying description and examples.

DESCRIPTION OF THE INVENTION

One or more objects of the present invention are accomplished by the provision of a novel class of pharmacologically active 4-substituted 2-iminoimidazolidine derivatives. Illustrative of the novel class of organic derivatives is a 2-iminoimidazolidine compound corresponding to the formula:

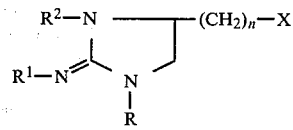

wherein R is alkyl; $R^1$ is a member selected from hydrogen, alkyl, aryl, alkylaryl and haloaryl; $R^2$ is a member selected from alkyl, aryl, alkylaryl, and haloaryl; X is a member selected from amino, alkylamino, aralkylamino, cycloamino, and halogen; and n is the integer 1 or 2.

The present invention also contemplates the pharmaceutically acceptable acid addition salts of the novel class of 4-substituted 2-iminoimidazolidine derivatives. Such salts have improved water solubility over the free bases. Typical acid addition salts are those derived from mineral acids such as hydrochloric, hydrobromic, sulfuric and phosphoric; and organic acids such as acetic, citric, lactic, maleic, oxalic, fumaric and tartaric. The preferred acid addition salt is the hydrochloride. The acid addition salts are conveniently prepared by reaction of the basic compounds with the selected acid, either or both of which may be in the form of ether, alcohol or acetone solutions.

The above described novel class of 4-substituted-2-iminoimidazolidine compounds, and particularly the acid addition salt derivatives thereof, are characterized by significant pharmacological activity, which is indicative of their application in counteracting certain physiological abnormalities in humans. The 4-substituted 2-iminoimidazolidine compounds possess varying degrees of hypotensive, nasal decongestant, antiarrhythmic, antisecretory, hypoglycemic (glucose tolerance), hypoglycemic (sugar cataract) and/or anti-inflammatory (pleural effusion) pharmacological activities.

In the above represented structural formula, the alkyl moiety in R, $R^1$, $R^2$ and X preferably is a lower alkyl radical containing between 1 and about 4 carbon atoms, e.g., methyl, ethyl, propyl, isopropyl, butyl and isobutyl.

The aryl moiety in $R^1$, $R^2$ and X as designated in the structural formula preferably is selected from phenyl and naphthyl radicals. Illustrative of alkylaryl substituents are mono- and di-substituted phenyl and naphthyl radicals such as tolyl, methylnaphthyl, dimethylphenyl, dimethylnaphthyl, propylphenyl, butylnaphthyl, and the like. Illustrative of aralkyl substituents are benzyl, phenethyl, phenpropyl, phenbutyl, naphthylmethyl, naphthylethyl, naphthylbutyl, and the like. The haloaryl substituent is preferably limited to fluoro, chloro, bromo or iodocontaining phenyl and naphthyl radicals.

Any of the aromatic nuclei enumerated above can contain, in addition to those mentioned, other radical substituents which are not reactive or otherwise interfering under the conditions of compound preparation. Such substituents include lower alkoxyl, trifluoromethyl, acetyl, and the like.

The alkylamino substituent designated in the structural formula preferably is a dialkylamino radical such as dimethylamino or dibutylamino. The aralkylamino substituent designated in the structural formula preferably is a di(aralkyl)amino radical, and most preferably is a di(phenylalkyl)amino radical such as dibenzylamino, di(phenethyl)amino, di(phenbutyl)amino, and the like.

The halogen substituent designated for X in the structural formula can be any of fluorine, chlorine, bromine and iodine, but preferably is a chloro radical.

The cycloamino substituent designated for X in the structural formula preferably is a five or six membered cycloaliphatic nucleus which can include other heteroatoms in addition to the amino nitrogen atom. Illustrative of cycloamines are pyrrolidino, alkylpyrrolidino, arylpyrrolidino, imidazolidino and substituted imidazolidino, piperidino, alkylpiperidino, arylpiperidino, morpholino, alkylmorpholino, arylmorpholino, piperazino, alkylpiperazino, arylpiperazino, 1,2,3,4-tetrahydroisoquinolyl, 1,2,5,6-tetrahydropyridino, 4-(2-pyridyl)piperazino, phthalimido, and the like.

With further reference to the aryl, alkylaryl and haloaryl substituents designated in the structural formula, the preferred substituents are hydrocarbon radicals containing a total between 6 and about 12 carbon atoms, respectively.

The preferred aralkylamino substituent is a di(arylkyl)amino radical in which each aralkyl group contains between 7 and about 10 carbon atoms. The preferred cycloamino substituent is a 1-cycloamino radical containing between 4 and about 12 carbon atoms.

Illustrative of specific 4-substituted 2-iminoimidazolidine compounds in accordance with the present invention are 4-(2-chloroethyl)-1-ethyl-2-imino-3-phenylimidazolidine; 1-ethyl-2-imino-4-(2-dimethylaminoethyl)-3-phenylimidazolidine; 1-ethyl-2-imino-4-[2-(1-morpholino)ethyl]-3-phenylimidazolidine; 4-(2-chloroethyl)-3-(p-chlorophenyl)-1-ethyl-2-iminoimidazolidine; 3-(p-chlorophenyl)-1-ethyl-2-imino-4-(2-dimethylaminoethyl)imidazolidine; 4-(2-chloroethyl)-1-ethyl-2-imino-3-(2,6-dimethylphenyl)imidazolidine; 4-(2-chloroethyl)-3-(3-chloro-4-methylphenyl-1-ethyl-2-iminoimidazolidine; 1-ethyl-2-imino-3-phenyl-4-[2-(1-piperidino)ethyl]imidazolidine; 4-(2-dibenzylaminoethyl)-1-ethyl-2-imino-3-phenylimidazolidine; 4-(2-aminoethyl)-1-ethyl-2-imino-3-phenylimidazolidine; 1-ethyl-4-[2-(3-ene-4-phenyl-1-piperidino)ethyl]-2-imino-3-phenylimidazolidine; 4-chloromethyl-2-imino-1-isopropyl-3-phenylimidazolidine; 1-ethyl-2-imino-4-[2-(4-methyl-1-piperazino)ethyl]-3-phenylimidazolidine; 4-(2-chloroethyl)-1-methyl-2-(methylamino-3-phenylimidazolidine; 4-(2-chloroethyl)-1,3-dimethyl-2-(phenylamino)imidazolidine; 4-(2-chloroethyl)-1-methyl-3-phenyl-2-(phenylimino)imidazolidine; 4-(2-chloroethyl)-2-(2,6-dichlorophenylimino)-1,3-dimethylimidazolidine; 4-(2-chloroethyl)-2-imino-1-methyl-3-phenylimidazolidine; 2-imino-1,3-dimethyl-4-(2-dimethylaminoethyl)imidazolidine; 4-(2-chloroethyl)-1-methyl-2-(2,6-dimethylphenylimino)-3-phenylimidazolidine; 2-imino-1-methyl-4-(2-dimethylaminoethyl)-3-phenylimidazolidine; 4-(2-chloroethyl)-2-isopropylimino)-1,3-dimethylimidazolidine; 1-ethyl-4-[2-(4-hydroxy-4-phenyl-1-piperidino)ethyl-2-imino-3-phenylimidazolidine; 3-(3-chloro-4-methylphenyl)-1-ethyl-2-imino-4-(2-dimethylaminoethyl)imidazolidine; and pharmaceutically acceptable acid addition salts thereof.

PREPARATION OF 4-SUBSTITUTED 2-IMINOIMIDAZOLIDINES

The invention 2-iminoimidazolidine compunds are readily prepared by conversion of suitable 2-imidazolidinone intermediates. A typical synthesis is illustrated by the following reaction scheme:

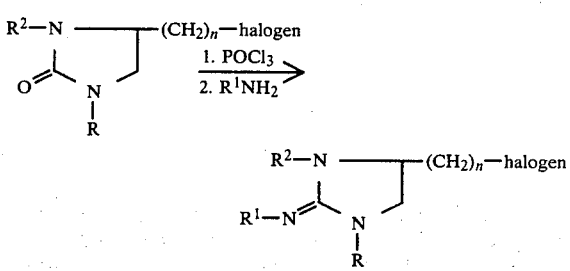

wherein R, $R^1$, $R^2$ and n are as previously defined, and the halogen is preferably a chloro radical.

A further transformation of the 2-iminoimidazolidine product illustrated above is accomplished by interaction of the product with ammonia or a selected organic amine compound:

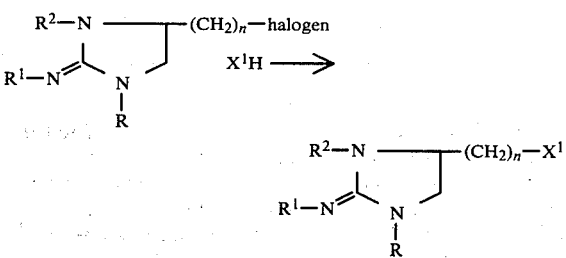

wherein R, $R^1$, $R^2$ and n are as previously defined, and $X^1$ is one of amino, alkylamino, aralkylamino and cycloamino radicals.

The preparation of a 2-imidazolidinone starting material is illustrated by the following diagram with specific reference to the preparation of 4-(chloroethyl)-1-methyl-2-oxo-3-phenylimidazolidine (I):

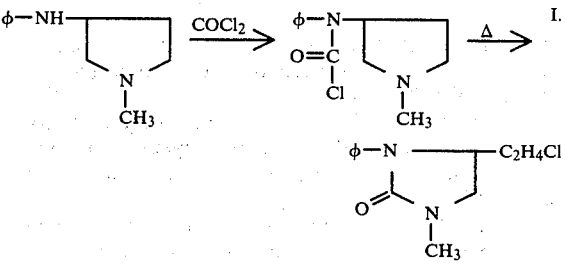

The preparation of 2-imidazolidinone derivatives in accordance with the above illustrated reaction scheme is described in detail in U.S. 3,337,580 incorporated herein by reference.

FORMULATION OF PHARMACEUTICAL COMPOSITIONS

In one embodiment, this invention provides a pharmaceutical composition for the treatment of cardiovascular hypertension comprising a pharmaceutical carrier and a hypertension inhibiting quantity of a 2-iminoimidazolidine compound corresponding to the formula:

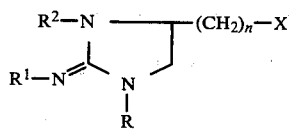

wherein R is alkyl; $R^1$ is a member selected from hydrogen, alkyl, phenyl, alkylphenyl, and chlorophenyl; $R^2$ is a member selected from alkyl, phenyl, alkylphenyl, and chlorophenyl; X is a member selected from amino, dialkylamino, di(phenylalkyl)amino, 1-piperidino, 1-piperazino, 1-morpholino, and chloro; and n is the integer 1 or 2.

Illustrative of 2-iminoimidazolidine compounds suitable for functioning as a hypertension inhibiting agent in the pharmaceutical composition described above are the pharmaceutically acceptable acid addition salts of 1-ethyl-2-imino-4-(2-dimethylaminoethyl)-3-phenylimidazolidine; 3-(4-chlorophenyl)-1-ethyl-2-imino-4-(2-dimethylaminoethyl)imidazolidine; 1-ethyl-2-imino-3-phenyl-4-[2-(1-piperidino)ethyl]imidazolidine; 4-[2-(dibenzylamino)ethyl]-1-ethyl-2-imino-3-phenylimidazolidine; 4-(2-aminoethyl)-1-ethyl-2-imino-3-phenylimidazolidine; 4-[2-(3-ene-4-phenyl-1-piperidino)ethyl-1-ethyl-2-imino-3-phenylimidazolidine; 1-ethyl-2-imino-4-[2-(4-methyl-1-piperazino)-ethyl]-3-phenylimidazolidine; 4-chloromethyl-2-imino-1-isopropyl-3-phenylimidazolidine; 4-(2-chloroethyl)-1-methyl-2-methylimino-3-phenylimidazolidine; and the like.

In another embodiment, this invention provides a pharmaceutical composition for the treatment of hyperglycemia comprising a pharmaceutical carrier and a hyperglycemia inhibiting quantity of a 2-iminoimidazolidine compound corresponding to the formula:

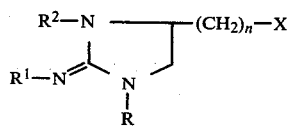

wherein R is alkyl; $R^1$ is a member selected from hydrogen, alkyl, phenyl, alkylphenyl, and chlorophenyl; $R^2$ is a member selected from alkyl, phenyl, alkylphenyl, and chlorophenyl; X is a member selected from amino, dialkylamino, di(phenylalkyl)amino, 1-piperidino, 1-piperazino, 1-morpholino, and chloro; and n is the integer 1 or 2.

Illustrative of 2-iminoimidazolidine compounds suitable as a hyperglycemia inhibiting agent in the pharmaceutical composition described above are the pharmaceutically acceptable acid addition salts of 4-(2-chloroethyl)-1-ethyl-2-imino-3-(2,6-dimethylphenyl)imidazolidine; 4-(2-chloroethyl)-1-methyl-2-methylimino-3-phenylimidazolidine; 4-(2-chloroethyl)-1-methyl-2-phenylimino-3-phenylimidazolidine; and the like.

In another embodiment, this invention provides a pharmaceutical composition for the treatment of cardiac arrhythmia comprising a pharmaceutical carrier and a cardiac arrhythmia inhibiting quantity of a 2-iminoimidazolidine compound corresponding to the formula:

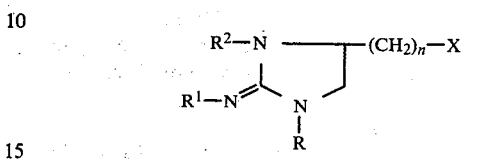

wherein R is alkyl; $R^1$ is a member selected from hydrogen, alkyl, phenyl, alkylphenyl, and chlorophenyl; $R^2$ is a member selected from alkyl, phenyl, alkylphenyl, and chlorophenyl; X is a member selected from amino, dialkylamino, di(phenylalkyl)amino, 1-piperidino, 1-piperazino, 1-morpholino, and chloro; and n is the integer 1 or 2.

Illustrative of 2-iminoimidazolidine compounds suitable as a cardial arrhythmia inhibiting agent in the pharmaceutical composition described above are the pharmaceutically acceptable acid addition salts of 4-(2-chloroethyl)-1-ethyl-2-imino-3-phenylimidazolidine; 4-(2-chloroethyl)-3-(4-chlorophenyl)-1-ethyl-2-iminoimidazolidine; 4-(2-chloroethyl)-1-ethyl-2-imino-3-(2,6-dimethylphenyl)imidazolidine; 4-(2-chloroethyl)-3-(3-chloro-4-methylphenyl)-1-ethyl-2-iminoimidazolidine; 4-(2-chloroethyl)-1,3-dimethyl-2-phenyliminoimidazolidine; and the like.

In a further embodiment, this invention provides a pharmaceutical composition for the treatment of sugar cataracts comprising a pharmaceutical carrier and a sugar cataract formation inhibiting quantity of a 2-iminoimidazolidine compound corresponding to the formula:

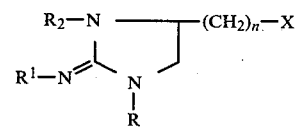

wherein R is alkyl; $R^1$ is a member selected from hydrogen, alkyl, phenyl, alkylphenyl, and chlorophenyl; $R^2$ is a member selected from alkyl, phenyl, alkylphenyl, and chlorophenyl; X is a member selected from amino, dialkylamino, di(phenylalkyl)amino, 1-piperidino 1-piperazino, 1-morpholino, and chloro; and n is the integer 1 or 2.

Illustrative of 2-iminoimidazolidine compounds suitable as a hyperglycemic sugar cataract formation inhibiting agent in the pharmaceutical composition described above are the pharmaceutically acceptable acid addition salts of 4-(2-chloroethyl)-1-ethyl-2-imino-3-(2,6-dimethylphenyl)imidazolidine; 4-(2-chloroethyl)-1-methyl-2-methylimino-3-phenylimidazolidine; 4-(2-chloroethyl-1,3-dimethyl-2-phenyliminoimidazolidine; 4-(2-chloroethyl)-1-methyl-3-phenyl-2-phenyliminoimidazolidine; 4-(2-chloroethyl)-2-(2,6-dichlorophenyl)imino-1,3-dimethylimidazolidine; 4-(2-chloroethyl)-2-imino-1-methyl-3-phenylimidazolidine, and the like.

The pharmaceutical compositions of the present invention are prepared in a form suitabe for administering to a living animal.

Pharmaceutical compositions for oral administration are preferably solids and can take the form of capsules, tablets or coated tablets containing carriers conveniently used in the pharmaceutical art. Suitable tableting excipients include lactose, potato and maize starches, talc, gelatin and stearic and silicic acids, magnesium stearate, and polyvinyl pyrrolidone.

For parenteral administration the carrier or excipient can be a sterile parenterally acceptable liquid (e.g., water), or a parenterally acceptable oil (e.g., arachis oil), contained in ampoules.

In compositions for rectal administration the carrier can comprise a suppository base such as cocoa butter or a glyceride.

Advantageously, the compositions are formulated as dosage units, each unit being adapted to supply a fixed dose of active ingredients. Tablets, coated tablets, capsules, ampoules and suppositories are examples of preferred dosage unit forms according to the invention. Each dosage unit adapted for oral administration may conveniently contain 10 to 40 mg. of the active ingredient; each dosage unit adapted for intracardial or intravenous administration may conveniently contain 1 to 2 mg. per cc of the active ingredient; whereas each dosage unit adapted for intramuscular administration may conveniently contain 5 to 10 mg per cc of the active ingredient.

Examples of compositions within the preferred ranges given are as follows:

| Capsules | |
|---|---|
| Ingredients | Per Cap. |
| 1. Active ingredient | 10.00 mg |
| 2. Lactose | 146.000 mg |
| 3. Magnesium stearate | 4.000 mg |

PROCEDURE

1. Blend 1, 2 and 3.
2. Mill this blend and blend again.
3. This milled blend is then filled into No. 1 hard gelatin capsules.

| Tablets | |
|---|---|
| Ingredients | Mg/Tab. |
| 1. Active ingredient | 10.0 mg |
| 2. Corn starch | 20.0 mg |
| 3. Kelacid | 20.0 mg |
| 4. Keltose | 20.0 mg |
| 5. Magnesium stearate | 1.3 mg |

PROCEDURE

1. Blend 1, 2, 3 and 4.
2. Add sufficient water portionwise to the blend from step 1 with careful stirring after each addition. Such additions of water and stirring continue until the mass is of a consistency to permit its conversion to wet granules.
3. The wet mass is converted to granules by passing it through the oscillating granulator, using 8-mesh screen.
4. The wet granules are then dried in an oven at 140° F.
5. The dried granules are then passed through an oscillating granulator, using a 10-mesh screen.
6. Lubricate the dry granules with 0.5% magnesium stearate.
7. The lubricated granules are compressed on a suitable tablet press.

| Intravenous Injection | |
|---|---|
| Ingredients | Per ml |
| 1. Active ingredient | 1.0 mg |
| 2. pH 4.0 Buffer solution q.s. to | 1.0 ml |

PROCEDURE

1. Dissolve the active ingredient in the buffer solution.
2. Aseptically filter the solution from step 1.
3. The sterile solution is now aseptically filled into sterile ampoules.
4. The ampoules are sealed under aseptic conditions.

| Intramuscular Injection | |
|---|---|
| Ingredients | Per ml |
| 1. Active ingredient | 5.0 mg |
| 2. Isotonic buffer q.s. to solution 4.0 | 1.0 ml |

PROCEDURE

1. Dissolve the active ingredient in the buffer solution.
2. Aseptically filter the solution from step 1.
3. The sterile solution is now aseptically filled into sterile ampoules.
4. The ampoules are sealed under aseptic conditions.

| Suppositories | |
|---|---|
| Ingredients | Per Supp. |
| 1. Active ingredient | 10.0 mg |
| 2. Polyethylene Glycol 1000 | 1350.0 mg |
| 3. Polyethylene Glycol 4000 | 450.0 mg |

PROCEDURE

1. Melt 2 and 3 together and stir until uniform.
2. Dissolve No. 1 in the molten mass from step 1 and stir until uniform.
4. Pour the molten mass from step 2 into suppository molds and chill.
4. Remove the suppositories from molds and wrap.

The following examples are further illustrative of the present invention. The reactants and other specific ingredients are presented as being typical, and various modifications can be devised in view of the foregoing disclosure within the scope of the invention.

PREPARATION A

This example illustrates the preparation of 3-anilino-1-methylpyrrolidine starting material.

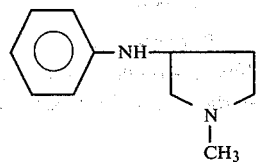

A dry toluene (1 liter) suspension of sodamide (2 moles) was placed in a 3-liter, 3-necked, round-bottomed flask equipped with a stirrer, reflux condenser, thermometer and dropping funnel. While maintaining the dispersion at a temperature of 15°–40° C., 1-methyl-3-pyrrolidinol (2 moles) was added dropwise. On completing the addition of the pyrrolidinol, the reaction mixture was stirred for two hours, gradually lowering the temperature to 10° C. A dry toluene (1 liter) solution of p-toluenesulfonyl chloride (2 moles) was added dropwise maintaining the temperature at less than 20° C. The reaction mixture was stirred for two hours at 20°–30° C. and then washed with cold water (2×500 ml). The toluene extract was dried over anhydrous calcium sulfate (Drierite). After removal of the drying agent, the toluene was removed by evaporation and the concentration tosylate was allowed to react with aniline (4.4 moles, 10% excess). Reaction of the aniline with the tosylate [(1-methyl-3-pyrrolidyl)-p-toluenesulfonate] was effected by heating at 150° C. for two hours and then raising the temperature to reflux and heating for an additional three hours. The excess unreacted aniline was removed under reduced pressure (water aspirator vacuum) and the remaining residue treated with a sufficient amount of cold dilute hydrochloric acid to effect solution. The acid solution was extracted several times with ethyl ether, cooled, and made basic with 50% aqueous sodium hydroxide. The free base was removed by extraction with ether. The other extracts were washed with water and dried over Drierite (anhydrous calcium sulfate). The drying agent was removed by filtration and the ether removed under reduced pressure. The resultant residue was then distilled at reduced pressure. B.P. 124°–126° C. at 4 mm pressure. The product was obtained in 52% yield. The corresponding fumarate salt was obtained from dry isopropanol solvent; m.p. 143°–144° C.

Analysis: Calculated for $C_{15}H_{20}N_2O_4$: C,61.63; H,6.90; N,9.58. Found: C,61.58; H,7.07; N,9.47.

PREPARATION B

This example illustrates the preparation of 4-(2-chloroethyl)-1-methyl-2-oxo-3-phenylimidazoline starting material.

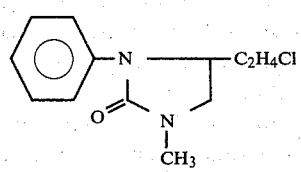

A solution of phosgene (0.88 mole) in chloroform (500 ml) was placed in a two-liter three-necked round-bottomed flask fitted with a stirrer, condenser, dropping funnel and thermometer, and cooled to zero °C. While stirring and maintaining the temperature at 10°–15° C., 3-anilino-1-methylpyrrolidine (0.44 mole) was added dropwise. On completing the addition of the substituted pyrrolidine, stirring was continued for two hours while the temperature rose to 25°–30° C. The temperature of the reaction mixture was then raised to reflux for a period of twelve hours. The reaction mixture was cooled to 0.5° C., and washed with hydrochloric acid (6 N, 200 ml). The chloroform layer was allowed to separate and then washed several times with water. The chloroform extracts were dried over anhydrous sodium sulfate, filtered, and the chloroform evaporated on a rotary steam evaporator under moderate reduced pressure. The isolated residue was purified by vacuum distillation under reduced pressure. The 2-imidazolidinone derivative exhibited a boiling range of 186°–190° C. at 0.1 mm Hg pressure (recrystallized from isopropyl ether; melting point 51°–52° C.) and was obtained in 86% yield based on the starting pyrrolidine.

Analysis: Calculated for $C_{12}H_{15}ClN_2O$: C,60.37; H,6.33; N,11.74; Cl,14.85. Found: C,60.40; H,6.44; N,11.71; Cl,14.75.

PREPARATION C

This example illustrates the preparation of 3-(2,6-dimethylanilino-1-ethyl-pyrrolidine starting material.

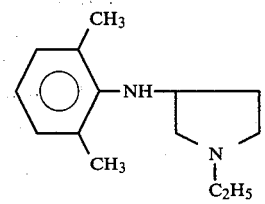

To 125 ml. of 2,6-dimethylaniline was added 60 g. (0.34 mole) of 3-bromo-1-ethylpyrrolidine and the resulting solution brought to reflux for 18 hours. The solution was then partitioned between chloroform and dilute sodium hydroxide. The chloroform layer was dried over $Na_2SO_4$, concentrated and distilled to yield 22 g. (29%) of product exhibiting a boiling range of 120°–130° C. at 0.2 mm Hg pressure.

PREPARATION D

This example illustrates the preparation of 4-(2-chloroethyl)-1-ethyl-3-(2,6-dimethylphenyl)-2-oxo-imidazolidine starting material.

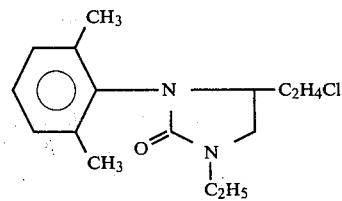

A solution of 10.9 g. (0.11 mole) of phosgene in 100 ml of chloroform was placed in an ice bath and 21 g. (0.096 mole) of 3-(2,6-dimethylanilino)-1-ethylpyrrolidine was added dropwise with stirring to the solution. The resulting solution was brought to reflux for 2.5 hours, allowed to cool, and placed in an ice bath. To this solution was added 10 g (0.1 mole) of triethylamine and the mixture was stirred at room temperature for 0.5 hour. The chloroform layer was extracted with dilute HCl followed by dilute NaOH. The chloroform extract was dried over $Na_2SO_4$, concentrated and distilled to yield 19.2 g (72%) of product exhibiting a boiling range of 175°–180° C. at 0.1 mm Hg pressure.

Example 1

Preparation of 4-(2-Chloroethyl)-1-ethyl-2-imino-3-phenylimidazolidine Hydrochloride

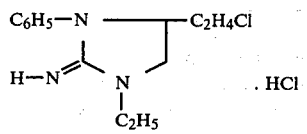

To 250 ml of phosphorus oxychloride was added 95.6 g (0.378 mole) of 4-(2-chloroethyl-1-ethyl-2-oxo-3-phenyl imidazolidine and the mixture stirred at 70°–100° C. for 3.5 hours and concentrated on the rotary evaporator, yielding an oil. The oil was added to approximately 500 ml of liquid ammonia and stirred while the ammonia was allowed to evaporate. The residue was partitioned between chloroform and dilute NaOH. The chloroform layer was concentrated and the residue dissolved in isopropyl ether. The isopropyl ether was treated with carbon black and filtered. The ether was made acidic with ethereal HCl and the resulting precipitate was collected by decanting the ether. The residue was crystallized from isopropyl alcohol and isopropyl ether. Yield 61 g (56%); m.p. 175°–177° C. Analytical sample recrystallized from isopropyl alcohol and isopropyl ether; m.p. 176°–177.5° C.

Analysis: Calculated for $C_{13}H_{19}N_3Cl_2$: C,54.17; H,6.64; N,14.57. Found: C,54.34; H,6.72; N,14.52.

Example 2

Preparation of 1-Ethyl-2-amino-4-(2-dimethylaminoethyl)-3-phenylimidazolidine Dihydrochloride

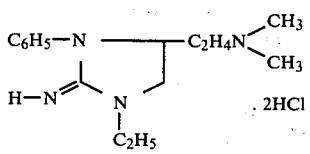

To a 9.4 g (0.21 mole) of dimethylamine in 200 ml ethanol was added 20 g (0.0695 mole) of 4-(2-chloroethyl)-1-ethyl-2-imino-3-phenylimidazolidine hydrochloride and the solution heated to 100° C. in a steel bomb for 18 hours. The contents were concentrated on the rotary evaporator and the resulting residue partitioned between chloroform and dilute NaOH. The chloroform solution was concentrated and the residue dissolved in isobutyl methyl ketone which was acidified with ethereal HCl. The resulting crystals were recrystallized from isopropanol-isobutyl methyl ketone. Yield 7.8 g (37.8%); m.p. 252°–254° C.

Analysis: Calculated for $C_{15}H_{26}N_4Cl_2$: C,54.05; H,7.86; N,16.81. Found: C,54.04; H,7.93; N,16.76.

EXAMPLE 3

Preparation of 4-(2-Chloroethyl)-3-(p-chlorophenyl)-1-ethyl-2-iminoimidazolidine Hydrochloride

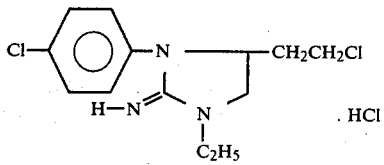

A solution of 15.0 g (0.09 mole) of 4-(2-chloroethyl)-3-(p-chlorophenyl)-1-ethyl-2-oxo-imidazolidine in 50 ml of phosphorus oxychloride was refluxed 3.5 hour and concentrated in vacuo. The residue was added dropwise into 100 ml of stirring liquid ammonia. The ammonia was allowed to evaporate overnight. The residue was partitioned between 150 ml of ethyl acetate and 150 ml of a 10% solution of NaOH. The acetate layer was dried over $Na_2SO_4$ and filtered. Ethereal HCl was added until the solution had precipitated the salt and tested acidic to litmus paper. The salt was recrystallized from ethyl acetate with a few drops of isopropanol added. The solid weighed 11.5 g (40% yield); m.p. 169°–170° C.

Analysis: Calculated for $C_{13}H_{18}Cl_3N_3$: C,48.39; H,5.62; N,13.02. Found: C,48.19; H,5.72; N,12.83.

Example 4

Preparation of 3-(4-Chlorophenyl)-1-ethyl-2-imino-4-(2-dimethyliminoethyl)imidazolidine Dioxalate

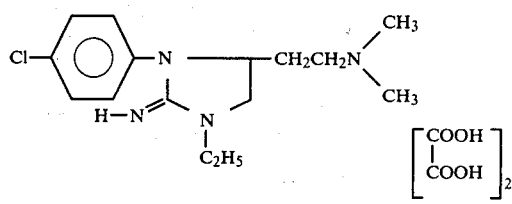

A solution of 23.0 g (0.08 mole) of 4-(2-chloroethyl)-3-(4-chlorophenyl)-1-ethyl-2-iminoimidazolidine hydrochloride in 200 ml of ethanol and 10.8 g (0.24 mole) of dimethylamine was heated in a steel bomb at 100° C. for 18 hours. The solution was concentrated and the residue was partitioned between a 10% solution of NaOH and chloroform. The chloroform layer was dried over $Na_2SO_4$, filtered, and concentrated in vacuo. The residue was dissolved in ethanol and 7.2 g (0.08 mole) of oxalic acid was added. The resulting dioxalate salt was recrystallized from boiling ethanol with a few drops of water added. The solid weighed 19.0 g (81% yield); m.p. 168°–171° C.

Analysis: Calculated for $C_{19}H_{27}ClN_4O_8$: C,48.06; H,5.73; N,11.80. Found: C,48.26, H,5.90; N,11.63.

Example 5

Preparation of
4-(2-Chloroethyl)-1-ethyl-3-(2,6-dimethylphenyl)-2-imidazolidineimine Hydrochloride

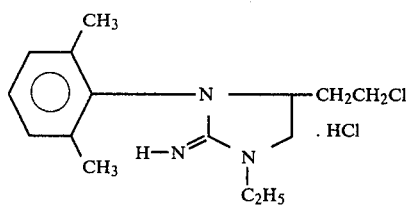

A solution of 28 g. (0.1 mole) of 4-(2-chloroethyl)-1-ethyl-3-(2,6-dimethylphenyl)-2-imidazolidinone in 150 ml of phosphorous oxychloride was refluxed 18 hours and concentrated in vacuo on the steam bath. The residue was dissolved in 30 ml of methylene chloride and added dropwise to 200 ml of boiling ammonia. The ammonia was allowed to evaporate and the residue was partitioned between chloroform and aqueous potassium carbonate. The chloroform solution was concentrated and the residue dissolved in isobutyl methyl ketone. The solution was acidified with ethereal hydrogen chloride and the resulting oil was stirred until it crystallized. The crystals were recrystallized twice by dissolving them in about 90% isobutyl methyl ketone—10% isopropyl alcohol and boiling until the solution becomes cloudy (addition of isobutyl methyl ketone may be necessary) and allowing this to cool. Yield 7.5 g (27%), m.p. 210°–212° C.

Analysis: Calculated for $C_{15}H_{23}N_3Cl_2$: C,56.96; H,7.33; N,13.29. Found: C,57.28; H,7.50; N,13.25.

Example 6

Preparation of
4-(2-Chloroethyl)-3-(3-chloro-4-methylphenyl)-1-ethyl-2-iminoimidazolidine Hydrochloride

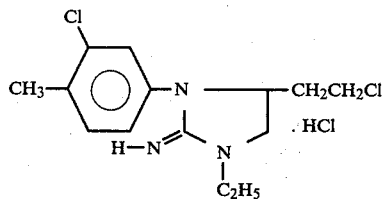

A solution of 30.0 g (0.10 mole) of 4 (2-chloroethyl)-3-(3-chloro-4-methylphenyl)-1-ethyl-2-oxoimidazolidine in 175 ml of phosphorus oxychloride was refluxed 56 hours. The solution was concentrated in vacuo, and the residue was added dropwise into stirring liquid ammonia. The ammonia was allowed to evaporate. The residue was partitioned between 150 ml of a 10% solution of hydrochloric acid and 150 ml of chloroform. The acid solution was made basic to litmus paper with a 10% solution of sodium hydroxide, and was extracted with an equal amount of chloroform. The solution was dried over sodium sulfate, filtered, and concentrated in vacuo. The residue was dissolved in ethyl acetate and a hydrochloride salt was made by the addition of ethereal HCl until the mixture was acid to litmus paper. The salt was recrystallized in ethyl acetate. The off-white solid weighed 7.0 g (21% yield); m.p. 225°–226° C.

Analysis: Calculated for $C_{14}H_{20}Cl_3N_3$: C,49.94; H,5.99; N,12.48. Found: C,49.77; H,5.90; N,12.31.

Example 7

Preparation of
1-Ethyl-2-imino-3-phenyl-4-[2-(1-piperidino)ethyl-]imidazolidine Dihydrochloride

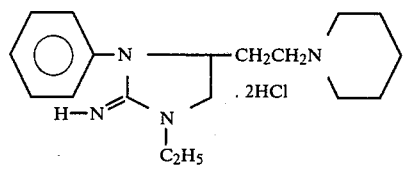

With piperidine as the solvent, a solution of 20.0 g (0.069 mole) of 4-(2-chloroethyl)-1-ethyl-2-imino-3-phenyl imidazolidine hydrochloride was refluxed for 2 hours and concentrated. The residue was partitioned between chloroform and a potassium carbonate solution. The chloroform layer was dried ($Na_2SO_4$), filtered and concentrated. The residue was dissolved in methyl isobutyl ketone, and ethereal HCl and added to form a salt. It was crystallized twice from ethanol, and weighed 13.5 g (58% yield) m.p. 270° C. (dec.).

Analysis: Calculated for $C_{18}H_{30}Cl_2N_4$: C,57.91; H,8.10; N,15.01. Found: C,57.45; H,8.08; N,14.88.

Example 8

Preparation of
4-(2-Dibenzylaminoethyl)-1-ethyl-2-imino-3-phenylimidazolidine Hydrochloride Monohydrate

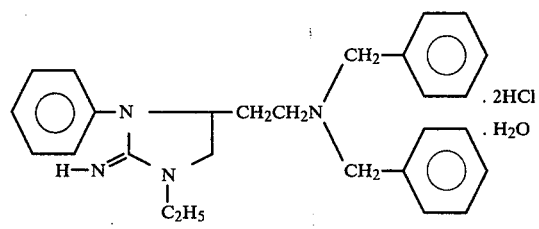

With Dibenzylamine as the solvent, 28.7 g (0.10 mole) of 4-(2-chloroethyl)-1-ethyl-2-imino-3-phenylimidazolidine hydrochloride was refluxed for 2 hours and concentrated in vacuo. After partitioning between a dilute potassium carbonate solution and chloroform, the chloroform layer was dried ($Na_2SO_4$), filtered, and concentrated in vacuo. After dissolving the residue in a 50% mixture of methyl isobutyl ketone and isooctane, a salt was formed with ethereal HCl. The salt was recrystallized twice from a 50% solution of ethyl acetate and isopropanol, and weighed 4.18 g (30% yield); m.p. 207°–208° C.

Analysis: Calculated for $C_{27}H_{36}Cl_2N_4O$: C,64.41; H,7.21; N,11.13. Found: C,64.72; H,7.04; N,11.03.

EXAMPLE 9

Preparation of 4-(2-Aminoethyl)-1-ethyl-2-imino-3-phenylimidazolidine Dihydrochloride

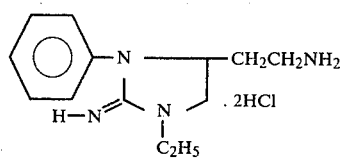

A solution of 10.0 g (0.023 mole) of 4-(2-dibenzylaminoethyl)-1-ethyl-2-imino-3-phenylimidazolidine dihydrochloride hydrate in 175 ml of ethanol was shaken for 7 hours in a Parr apparatus at 70° C. with palladium catalyst at 45 p.s.i. hydrogen. After filtering and concentrating the filtrate in vacuo, the solid residue was recrystallized from a 80/20% mixture of isopropanol-ethanol. The salt weighed 4.55 g (70% yield); m.p. 223°–224° C.

Analysis: Calculated for $C_{13}H_{22}Cl_2N_4$: C, 51.15; H, 7.27; N, 18.35. Found: C, 50.99; H, 7.22; N, 18.02.

EXAMPLE 10

Preparation of 4-[2-(3-Ene-4-phenyl-1-piperidino)ethyl]-1-ethyl-2-imino-3-phenylimidazolidine Dihydrochloride Monohydrate

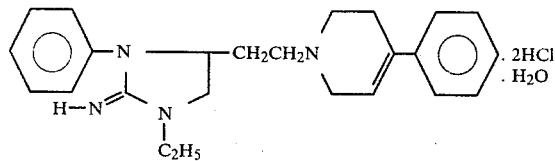

By partitioning between chloroform and a dilute sodium hydroxide solution, 16.0 g (0.10 mole) of 1,2,5,6-tetrahydro-4-phenylpyridine hydrochloride was converted to the free base and dissolved in 125 ml of dry toluene. To this 14.3 g (0.05 mole) of 4-(2-chloroethyl)-1-ethyl-2-imino-3-phenylimidazolidine hydrochloride was added, and the solution was refluxed for 2 hours and concentrated in vacuo. The residue was partitioned between a dilute hydrochloric acid solution and ethyl acetate, and the acid layer was then made basic with a dilute potassium carbonate solution and extracted with ethyl acetate. Ethereal hydrogen chloride was added until a salt formed, which was recrystallized from a 50% solution of isopropyl alcohol and ethyl acetate and weighed 5.4 g (24% yield); m.p. 236°–239° C. (dec).

Analysis: Calculated for $C_{24}H_{34}Cl_2N_4O$: C, 62.93; H, 7.36; N, 12.04. Found: C, 62.90; H, 7.09; N, 12.02.

EXAMPLE 11

Preparation of 1-Ethyl-2-imino-4-[2-(4-methyl-1-piperazino)ethyl]-3-phenylimidazolidine Trihydrochloride Monohydrate

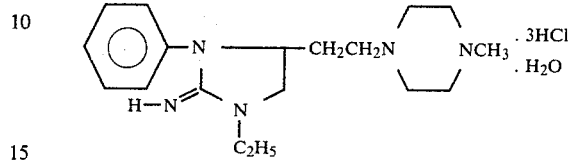

With methylpiperazine as the solvent, 14.5 g (0.05 mole) of 4-(2-chloroethyl-1-ethyl-2-imino-3-phenylimidazolidine hydrochloride was refluxed for two hours. The solution was concentrated in vacuo, and the residue was partitioned between chloroform and a dilute potassium carbonate solution. The chloroform layer was dried ($Na_2SO_4$), filtered and concentrated in vacuo. The residue was dissolved in ethyl acetate and treated with ethereal HCl until acidic and a salt precipitated. It was recrystallized twice from a mixture of ethyl acetate and isopropanol, and weighed 4.0 g. (20% yield); m.p. 260°–262° C.

Analysis: Calculated for $C_{18}H_{34}Cl_3N_5O$: C, 48.82; H, 7.74; N, 15.81. Found: C, 49.07; H, 7.53; N, 15.46.

EXAMPLE 12

Preparation of 4-(2-Chloroethyl)-1-methyl-2-(methyl imino)-3-phenylimidazolidine Fumarate

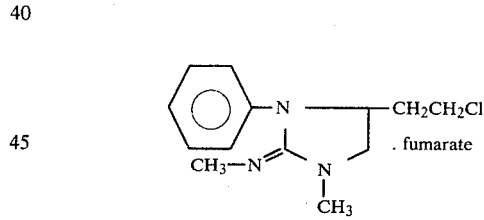

To 50 ml of $POCl_3$ was added 15 g (0.062 mole) of 4-(2-chloroethyl)-1-methyl-2-oxo-3-phenylimidazolidine and the solution refluxed for 18 hours and concentrated. The residue was dissolved in 50 ml of $CH_2Cl_2$ and added dropwise with stirring and dry ice bath cooling (about −20° C.) to 50 ml of methylamine. The mixture was stirred about 2 hours while the excess methylamine evaporated. The residue was extracted with a saturated $NaHCO_3$ solution. The $CH_2Cl_2$ solution was dried ($Na_2SO_4$) and concentrated. The resulting concentrate was distilled at about 180° C./0.01 mm Hg. The distillate was treated with fumaric acid in isopropanol to yield the salt product; m.p. 133°–135° C.

Analysis: Calculated for $C_{17}H_{22}ClN_3O_4$: C, 55.51; H, 6.03; N, 11.42. Found: C, 55.91; H, 6.13; N, 11.42.

EXAMPLE 13

Preparation of 4-(2-chloroethyl)-1,3-dimethyl-2-phenyliminoimidazolidine Fumarate

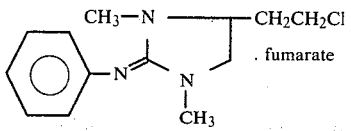

To 8.0 g (0.045 mole) of 4-(2-chloroethyl)-1,3-dimethyl-2-oxo-imidazolidine was added 50 ml of phosphorus oxychloride, and the solution was refluxed for 18 hours, and concentrated in vacuo. The residue was dissolved in 25 ml of methylene chloride and added dropwise to 4.2 g (0.045 mole) of aniline stirring at room temperature. Stirring was continued for two hours. The solution was diluted with chloroform and washed with dilute sodium hydroxide solution. The chloroform was dried, filtered and concentrated in vacuo. The residue was dissolved in isopropyl alcohol and treated with 5.2 g. (0.045 mole) fumaric acid, and the resulting fumarate was recrystallized from isopropyl alcohol and weighed 9.0 g (50% yield); m.p. 109°–112° C.

Analysis: Calculated for $C_{17}H_{22}ClN_3O_4$: C, 55.51; H, 6.03 N, 11.42. Found: C, 55.42; H, 6.01; N, 11.36.

EXAMPLE 14

Preparation of 4-(2-Chloroethyl)-1-methyl-3-phenyl-2-phenyliminoimidazolidine Fumarate

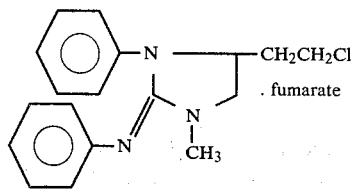

To 23.0 g (0.1 mole) of 4-(2-chloroethyl)-1-methyl-2-oxo-3-phenylimidazolidine was added 150 ml of phosphorus oxychloride, and the solution was refluxed for 18 hours. After concentrating in vacuo, the residue was dissolved in 20 ml of methylene chloride and added dropwise to a stirring solution of 9.0 g (0.10 mole) of aniline in methylene chloride. The solution was stirred at room temperature for one hour and washed with a dilute 10% sodium hydroxide. The methylene chloride layer was then dried, filtered, and concentrated in vacuo. The residue was dissolved in isopropanol and treated with 11.6 g. of fumaric acid, and the resulting salt was recrystallized twice from ethanol and weighed 12.0 g (28% yield); m.p. 136°–137° C.

Analysis: Calculated for $C_{22}H_{24}N_3O_4$: C, 61.47; H, 5.63; N, 9.77. Found: C, 61.17; H, 5.62; N, 9.66.

EXAMPLE 15

Preparation of 4-(2-Chloroethyl)-2-(2,6-dichlorophenylimino)-1,3-dimethylimidazolidine Sesquifumarate

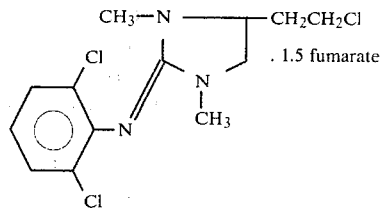

To 26.0 g (0.148 mole) of 4-(2-chloroethyl)-1,3-dimethyl-2-oxoimidazolidine was added 125 ml of phosphorous oxychloride, and the solution was refluxed overnight. After concentrating in vacuo, the residue was dissolved in methylene chloride, 15.0 g of triethylamine was added, and this solution was dropped into 24.0 g (0.148 mole) of 2,5-dichloroaniline, while stirring at room temperature. Stirring was continued for two hours. After washing with a dilute potassium bicarbonate solution, the organic layer was dried, filtered and concentrated in vacuo. The residue was dissolved in 50% isopropyl ether-50% isopropyl alcohol. Hydrogen chloride was added, producing the hydrochloride salt of the excess dichloroaniline which was removed by filtration. The filtrate was concentrated in vacuo and the residue partitioned between a dilute hydrochloric acid solution and ethyl acetate. The acid layer was made basic with a dilute sodium bicarbonate solution and extracted with chloroform, which was dried, filtered, and concentrated in vacuo. The residue was columned on Florisil using 20 to 30% methanol in benzene to remove the product from the column. After concentrating the combined fractions in vacuo, the residue was dissolved in isopropanol alcohol and treated with fumaric acid (1.5 g) and recrystallized from the same. Yield 2.0 g (3%); m.p. 162°–164° C.

Analysis: Calculated for $C_{19}H_{22}Cl_3N_3O_6$: C, 46.13; H, 4.48; N, 8.49. Found: C, 46.05; H, 4.55; N, 8.32.

EXAMPLE 16

Preparation of 4-(2-Chloroethyl)-2-imino-1-methyl-3-phenylimidazolidine Hydrochloride

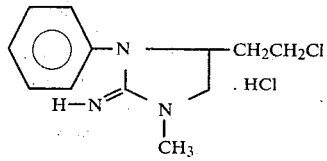

To 23.8 g (0.10 mole) of 4-(2-chloroethyl)-1-methyl-2-oxo-3-phenylimidazolidine was added 125 ml of phosphorus oxychloride, and the solution was refluxed overnight. Upon concentrating in vacuo, the residue was dissolved in methylene chloride and added dropwise to 150 ml of stirring liquid ammonia. After all the liquid had evaporated, the resulting residue was partitioned between ice-cold potassium bicarbonate solution and chloroform. The organic layer was dried, filtered and concentrated in vacuo. The residue was dissolved in ethyl acetate and treated with ethereal hydrogen chloride. The salt was recrystallized from ethyl acetate-ethanol (3:1) and weighed 9.34 g (34% yield); m.p. 220°–222° C.

Analysis: Calculated for $C_{12}H_{17}Cl_2N_3$: C, 52.57; H, 6.25; N, 15.33. Found: C, 52.34; H, 6.29; N, 15.23.

EXAMPLE 17

Preparation of 2-Imino-1,3-dimethyl-4-(2-dimethylaminoethyl-)imidazolidine Dihydrochloride Hydrate (4:1)

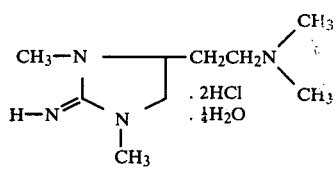

To 10.0 g (0.047 mole) of 4-(2-chloroethyl)-2-imino-1,3-dimethylimidazolidine hydrochloride was added 6.8 g (0.15 mole) of dimethylamine in 175 ml of methanol. The mixture was heated in a steel bomb at 100° C. for 15 hours. After concentrating in vacuo, the residue was partitioned between a dilute sodium carbonate solution and chloroform. The organic layer was dried ($Na_2SO_4$), filtered, and concentrated in vacuo. The residue was dissolved in ethyl acetate and treated with ethereal HCl. The hydrochloride was recrystallized from ethanol twice, and weighed 3.2 g (26% yield); m.p. 210°–212° C.

Analysis: Calculated for $C_{36}H_{90}Cl_8N_{16}O$: C, 41.31; H, 8.67; N, 21.41. Found: C, 41.49; H, 8.80; N, 21.51.

EXAMPLE 18

Preparation of 4-Chloromethyl-2-imino-1-isopropyl 3-phenylimidazolidine Fumarate

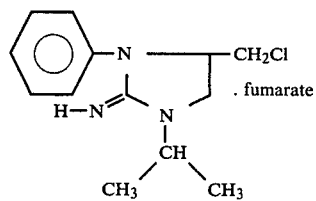

A

To a stirring solution of 92.4 (1.10 mole) of sodium bicarbonate in 250 ml of water was slowly added 100.0 g (0.35 mole) of 1-isopropyl-3-azetidinylmethane sulfonate oxalate. To the above was added 250 ml of aniline and the solution was refluxed for three hours. After cooling, the solution was extracted with ethyl acetate, and the acetate layer was dried ($Na_2SO_4$), filtered and concentrated in vacuo. The residue was distilled at 100°–110° C./0.1 mm Hg. Yield 38.8 g (58%). Five grams were dissolved in isopropyl alcohol and treated with ethereal HCl. The resulting salt was recrystallized from ethanol. The yield of 3-anilino-1-isopropyl-azetidine hydrochloride hemihydrate was 6 g.

B

To a stirring cooled solution of 17.2 g (0.176 mole) of phosgene in 250 ml of chloroform was added dropwise, 30.0 g (0.16 mole) of 3-anilino-1-isopropylazetidine. The solution was refluxed two hours, and 19.4 g (0.19 mole) of triethylamine was added at room temperature. Stirring was continued for one hour. The chloroform was washed with dilute HCl and then with dilute NaOH solution. After drying with $Na_2SO_4$, filtering and concentrating in vacuo, the residue was distilled at 172°–175° C./0.1 mm Hg. Yield 39.0 g (97%). Crystals formed upon standing and were recrystallized from isopropyl ether. There was obtained 21.5 g (53%) of 4-chloromethyl-1-isopropyl-2-one-3-phenyl imidazolidine product; m.p. 61°–63° C.

C

A stirring solution of 16.0 g (0.063 mole) of 4-chloromethyl-1-isopropyl-2-oxo-3-phenylimidazolidine in 200 ml of phosphorus oxychloride was refluxed for three hours and concentrated in vacuo. The residue was dissolved in 20 ml of methylene chloride and the solution dropped into stirring liquid ammonia. The ammonia was allowed to evaporate. The residue was partitioned between dilute HCl and isopropyl ether. The acid layer was made basic with dilute sodium carbonate solution and was extracted with chloroform. The organic layer was dried ($Na_2SO_4$), filtered and concentrated in vacuo. The residue which weighed 7.0 g was treated with an equivalent of fumaric acid in isopropyl alcohol. The salt was recrystallized from ethanol. The recovered 4-chloromethyl-2-imino-1-isopropyl-3-phenylimidazolidine fumarate product weighed 8.0 g (31% yield); m.p. 170°–171° C.

Analysis: Calculated for $C_{17}H_{22}ClN_3O_4$: C, 55.51; H, 6.03; N, 11.42. Found: C, 55.50; H, 6.07; N, 11.41.

What is claimed is:

1. A method for the treatment of sugar cataracts in a patient comprising administering a pharmaceutical carrier and a sugar cataract formation inhibiting quantity of a 2-iminoimidazolidine compound corresponding to the formula:

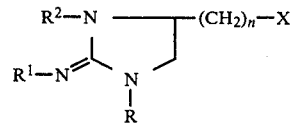

wherein R is loweralkyl; $R^1$ is a member selected from hydrogen, loweralkyl, phenyl, loweralkyl phenyl, and chlorophenyl; $R^2$ is a member selected from loweralkyl, phenyl, loweralkylphenyl, and chlorophenyl; X is a member selected from amino, diloweralkylamino, di(-phenylloweralkyl)amino, 1-piperidino, 1-piperazino, 1-morpholino, and chloro; and n is the integer 1 or 2, or a pharmaceutically acceptable acid addition salt thereof.

2. The method in accordance with claim 1 wherein the 2-iminoimidazolidine compound is 4-(2-chloroethyl)-1-ethyl-2-imino-3-(2,6-dimethylphenyl)imidazolidine or a pharmaceutically acceptable acid addition salt thereof.

3. The method in accordance with claim 1 wherein the 2-iminoimidazolidine compound is 4-(2-chloroethyl)-1-methyl-2-methylimino-3-phenylimidazolidine or a pharmaceutically acceptable acid addition salt thereof.

4. The method in accordance with claim 1 wherein the 2-iminoimidazolidine compound is 4-(2-chloroethyl)-1,3-dimethyl-2-phenyliminoimidazolidine or a pharmaceutically acceptable acid addition salt thereof.

5. The method in accordance with claim 1 wherein the 2-iminoimidazolidine compound is 4-(2-chloroethyl)-1-methyl-3-phenyl-2-phenyliminoimidazolidine or a pharmaceutically acceptable acid addition salt thereof.

6. The method in accordance with claim 1 wherein the 2-iminoimidazolidine compound is 4-(2-chloroethyl)-2-(2,6-dichlorophenylimino)-1,3-dimethylimidazolidine or a pharmaceutically acceptable acid addition salt thereof.

7. The method in accordance with claim 1 wherein the 2-iminoimidazolidine compound is 4-(2-chloroethyl)-2-imino-1-methyl-3-phenylimidazolidine or a pharmaceutically acceptable acid addition salt thereof.

* * * * *